United States Patent [19]

Zellweger

[11] Patent Number: 5,136,461
[45] Date of Patent: Aug. 4, 1992

[54] APPARATUS FOR STERILIZING AND DEODORIZING ROOMS HAVING A GROUNDED ELECTRODE COVER

[76] Inventor: Max Zellweger, Alte Wollerauerstrasse 36, CH-8805 Richterswil, Switzerland

[21] Appl. No.: 362,359

[22] Filed: Jun. 7, 1989

[30] Foreign Application Priority Data

Jun. 7, 1988 [CH] Switzerland .................... 2163/88

[51] Int. Cl.⁵ .................... H01T 23/00; H05F 3/06
[52] U.S. Cl. .................... 361/231; 55/150; 55/155; 422/121
[58] Field of Search .............. 361/231, 232, 380, 392, 361/393, 394, 395, 399, 424, 235, 230, 331; 55/146, 150, 155, 138, 139; 422/120, 121, 187; 174/52.2

[56] References Cited

U.S. PATENT DOCUMENTS

| | | | |
|---|---|---|---|
| 4,096,544 | 6/1978 | Ignatjev | 361/231 |
| 4,480,284 | 10/1984 | Tojo et al. | 361/230 |
| 4,496,375 | 1/1985 | Le Vantine | 361/230 |
| 4,533,598 | 8/1985 | Downey et al. | 174/52.2 |
| 4,589,053 | 5/1986 | Hosono et al. | 361/230 |
| 4,792,680 | 12/1988 | Lang et al. | 361/230 |

*Primary Examiner*—A. D. Pellinen
*Assistant Examiner*—Richard Elms
*Attorney, Agent, or Firm*—Christa Hildebrand

[57] ABSTRACT

An apparatus for sterilizing and deodorizing rooms comprises a circuit part and an ionization part. High voltage of up to 3 kV necessary for forming corona discharges is produced in the circuit part. The ionization part comprises electrodes, which are arranged on both sides of an insulator plate. An electron emission is produced on the second in operation, which leads to negative oxygen ions, which destroy bacteria and spores and remove odors from the air.

25 Claims, 2 Drawing Sheets

APPARATUS FOR STERILIZING AND DEODORIZING ROOMS HAVING A GROUNDED ELECTRODE COVER

BACKGROUND OF THE INVENTION

The present invention relates to an apparatus for sterilizing and deodorizing rooms, particularly those which are linked with cooling and refrigerating plants. Such apparatus has an insulator and two facing electrodes mounted on the latter. A high voltage is applied to the electrodes for the formation of a corona discharge.

Numerous different constructions of room sterilizing apparatus are known. With widely varying constructions, such devices particularly produce ozone ($O_3$), which has an indirect, sterilizing action. However, ozone is one of the most powerful oxidizing agents, which attacks the mucosa of the human organism, particularly the respiratory tracks and leads to unpleasant irritations.

For producing atmospheric ionization, use is made of discharge tubes in which an electrode is applied to an insulator, usually a glass tube. The electrode is applied to both the inner and the outer wall. High voltage is applied to these two facing electrodes, which leads to discharge coronas with a corresponding electron emission.

A process and an apparatus have been known for producing corona discharges in air, in which use is made of an insulator tube, in whose interior close to the inner wall is provided a first tubular electrode. A second tubular electrode is placed on the outer wall of the insulator tube and is formed from a wire gauze or lattice and on which, following the application of a high voltage, coronas occur, which leads to an atmosphere ionization. In the case of this known apparatus, atmospheric ionization takes place in the form of oxygen clusters, whose compatibility is greater than that of ozone ($O_3$).

However, as the insulator tubes and the transformer associated therewith, together with its control system, take up a relatively large volume, such apparatuses cannot be used in smaller rooms, such as for refrigerators. They can also not be used because there is a prescribed protection against electric shock hazard in view of the high voltage which is necessary for operation of such devices. Therefore the known apparatus is arranged in a casing and is used for disinfecting the air, deodorizing and conditioning spent air in larger rooms.

SUMMARY OF THE INVENTION

It is an object of the present invention to improve the air in smaller rooms by disinfection, deodorizing and conditioning through ionization thereof. A further object of the invention is to develop an apparatus of the aforementioned type so that it constitutes a small compact apparatus with excellent protection against electric shock hazard, whilst also being protected against temperature and moisture influences.

According to the invention this and other objects are attained by an apparatus in which the insulator, the two electrodes and the circuit for producing high voltage and high frequency are arranged in stacked and superimposed one on top of the other to fit compactly in a space to be sterilized and deodorized.

Appropriately, at least the circuit is embedded in a potting or sealing compound, e.g. of plastic. The apparatus is preferably parallelepipedic, the circuit, the electrodes and the insulator being arranged therein, the apparatus walls being formed by the electrode which is earthed.

The invention is described in greater detail hereinafter relative to an embodiment and the attached drawings.

DETAILED DESCRIPTION OF THE PREFERRED EMBODIMENT

The present invention is based on the idea that an apparatus for sterilizing rooms, where there are extreme conditions as regards temperature and moisture, can be reliably operated if all the sensitive parts are protected against those environmental factors and also if the official requirements concerning protection against electric shock hazard are fulfilled. In addition, the apparatus must have small dimensions, so that it takes up little space in the room to be sterilized.

Figure 1:
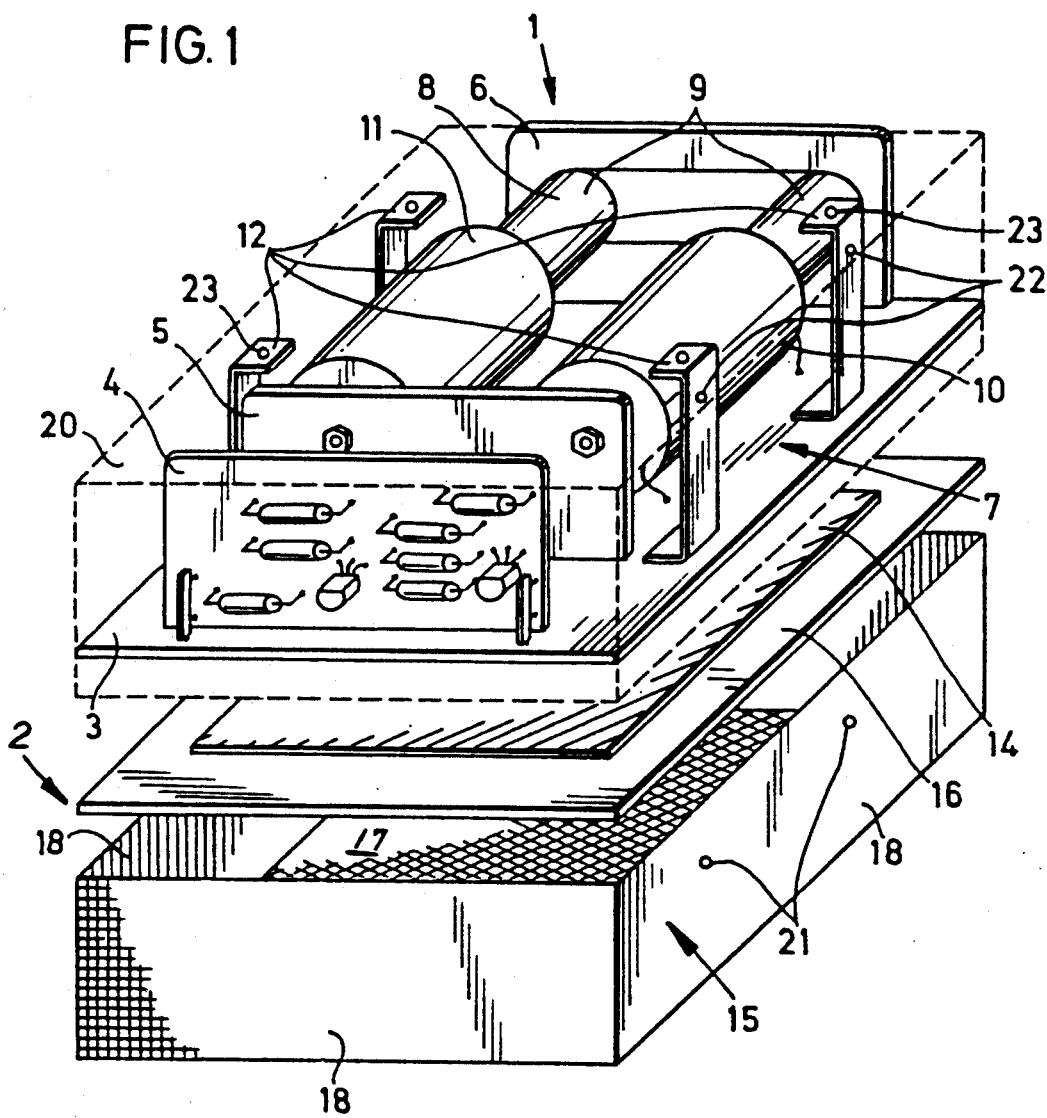
FIG. 1 is a diagrammatic perspective view of the apparatus according to the present invention, the parts of which are disassembled.

An apparatus according to the invention shown in FIG. 1, essentially comprises a circuit part 1 and an ionization part 2, which are together shaped in the form of a parallelepipedic body having a length and width of less than 10 cm and a height of less than 4 cm.

FIG. 1 shows the individual parts of the circuit superimposed in a stack laid one on top of the other to fit compactly in a space to be sterilized and deodorized in a or sandwich-like manner. On a basic printed circuit board 3 is arranged an electronic printed circuit board 4, which contains all the electronic components required for the operation of ionization part 2. The electronic printed circuit board 4 can also be integrated into the basic printed circuit board 3 so that only one board is then required.

A transformer 7 is fixed to two holding plates 5, and on its two legs 9 are arranged windings 10, 11, the primary winding 10 being arranged on one leg and the secondary winding 11 on the other.

On the basic printed circuit board 3 are supported assembly clips 12, with the aid of which the sterilizing apparatus can be fixed to a substrate. The assembly clips 12 are arranged on both sides of the basic printed circuit board 3, but could also be arranged in some other way. They are appropriately located within the surface of the basic circuit board 3. The assembly clips 12 can also be constructed as parts of a solid wall.

On the side of the basic printed circuit board 3 opposite to transformer 7 is provided a first electrode 14 of ionization part 2. The first electrode 14 is a solid or perforated, planar plate made from a metal, preferably selected from the group comprising steel, copper, aluminum and brass. However, the first electrode 14 can also be vapor deposited as a film on the potting compound surface. In an alternative embodiment not shown in FIG. 1, the first electrode is embedded with its free surface in a potting compound by a bonding means.

To the first electrode 14 is placed on insulator plate 16, which is made from an insulating material, e.g. glass or a plastic. As can be gathered from FIG. 1, the insulator plate 16 has somewhat larger dimensions than the first electrode 14 and therefore projects beyond the entire circumference of electrode 14.

Whereas the first electrode 14 is made from a relatively thin sheet or film, insulator plate 16 has a greater thickness, e.g. 0.5 to 4.0 mm.

To insulator plate 16 is placed a second electrode 15. The latter is made from a metal, preferably selected from the group comprising steel, copper, aluminum and brass, but is formed from wires of said metals and constitutes a screen or grid, at the meshes of which electrons are emitted on operating the apparatus and from negative oxygen ions on linking with oxygen atoms.

The second electrode 15 comprises a planar base surface 17 and side surfaces 18. The second electrode 15 consequently forms a dome covering not only ionization part 2, but also circuit part 1, cf. FIG. 3. To prevent the second electrode 15 from being contaminated by a liquid or some other material, it can be covered by a protective basket, which has openings, so that the electron emissions into the air are not impeded.

To ensure complete protection of the circuit part 1, it is completely slush moulded, for which purpose a slush moulding compound 20 is used. The latter is of a thermoplastic or thermosetting plastics material polyvinyl chloride and polyurethane which is cured after slush moulding. The slush moulding compound 20 extends up to the assembly clips 12 to envelope the same so that the clips 12 are partly embedded in the slush moulding compound, but are accessible to the extent that the second electrode 15 can be connected to the assembly clips 12 or the wall. For this purpose bores or tapholes 21, 22 are provided, with the aid of which the second electrode 15 is fastened to the assembly clips 12 or the wall. The assembly clips 12 or the wall are bent at their free ends and are provided at this point with bores 23. By means of said bores, the apparatus in the form of a parallelipiped or cube can be fixed to a substrate by bolts, said bolts and also the second electrode 15 being earthed, so that the official requirements concerning protection against electric shock hazard are fulfilled. The basic printed circuit board 3 can also be surrounded on both sides by the slush moulding compound 20.

Figure 2:
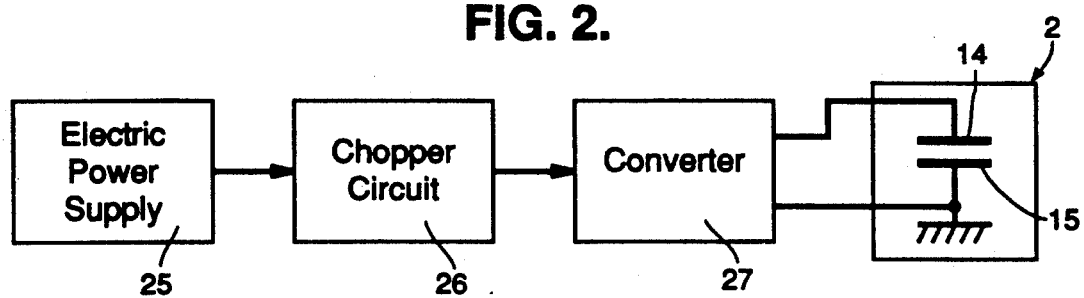
FIG. 2 is a block diagram of the circuit of the apparatus according to FIG. 1.

FIG. 2 shows a block diagram of the electronic circuit in connection with electrodes 14 and 15. By means of a converter or transformer 27, the voltage from an electric power supply 25, which is e.g. the 220 V mains or a d.c. source, is transformed to approximately 3 kV. The frequency required by the converter 27 is produced by a chopper circuit 26. This frequency is dependent on the ionization surface of the first electrode 15 of ionization part 2 and must be resonance tuned. Converter 27 can be a forward, resonance or push-pull converter, whose secondary circuit is constructed as a resonance circuit and which is connected by a first terminal to the first electrode 14 and by a second terminal to the protective earth. The necessary frequencies are approximately 10 kHz. The earthing of the second electrode 15 is indicated in the ionization part 2 shown diagrammatically in FIG. 2.

Figure 3:
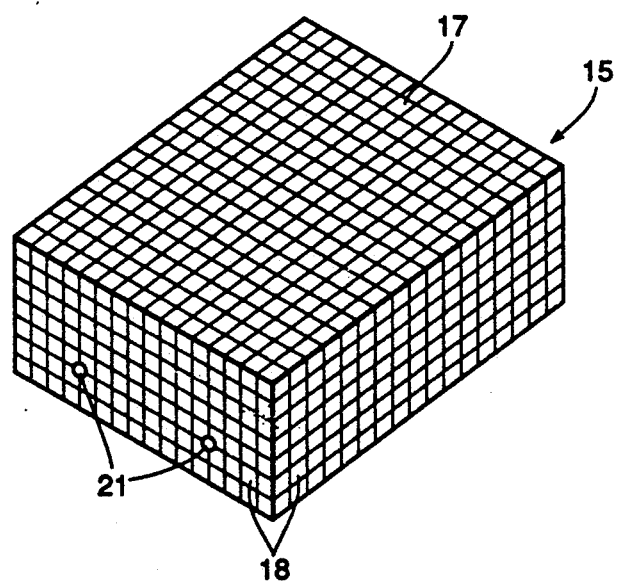
FIG. 3 is a perspective view of the apparatus according to FIG. 1.

FIG. 3 shows the external appearance of the whole sterilizing apparatus of the invention. It is possible to see the second electrode 15 with its base surface 17 and side surface covering the circuit part 1.

The described apparatus ensures troublefree operation in various rooms, e.g. in refrigerating and cooling rooms, as well as in cars, telephone kiosks and WC's. For an apparatus size of 90×90×35 mm a secondary power of 2W and a voltage of 3 kV are obtained. The ionization surface is 49 cm$^2$ and is essentially the active part of the first electrode 14. The electron emission occurring in operation produces negative ions, particularly oxygen ions. The latter are able to destroy bacteria and spores in the air, as well as neutralize odors and consequently prevent the transfer of odors, e.g. of onions or cheese to milk or cream.

There has been disclosed heretofore the best embodiment of the invention presently contemplated. However, it is to be understood that various changes and modifications may be made thereto without departing from the spirit of the invention.

What is claimed is:

1. In an apparatus for sterilizing and deodorizing rooms, including rooms having space inside cooled by refrigeration, comprising an ionization means having an insulator and two facing electrodes mounted to said insulator, and a circuit part for producing high voltage and high frequency applied to said electrodes for producing a corona discharge, the improvement comprising a second electrode being a cover which is constructed of a grounded metal web or grid for emitting electrons in surrounding airspace.

2. Apparatus according to claim 1, wherein at least the circuit part is embedded in a potting compound.

3. Apparatus according to claim 2, wherein said compound is of plastics material.

4. Apparatus according to claim 3, wherein said material is polyvinyl chloride.

5. Apparatus according to claim 3, wherein said material is polyurethane.

6. Apparatus according to claim 2, wherein said insulator is a substantially planar insulator plate on one side of which is mounted a first electrode made from metal and on the other side of which is mounted said second electrode made from metal.

7. Apparatus according to claim 6, wherein said first electrode of the ionization means is located on one side of a printed circuit board.

8. Apparatus according to claim 6, wherein said insulator plate is of glass.

9. Apparatus according to claim 6, wherein said insulator plate is of plastics.

10. Apparatus according to claim 6, wherein said first electrode is made of foil.

11. Apparatus according to claim 6, wherein said first electrode is in the shape of grid.

12. Apparatus according to claim 6, wherein said first electrode is made of metal selected from the group comprising steel, copper, aluminum and brass.

13. Apparatus according to claim 6, wherein said second electrode is formed as a perforated sheet.

14. Apparatus according to claim 6, wherein said second electrode is in the shape of grid.

15. Apparatus according to claim 6, wherein said second electrode is made of metal selected from the group comprising steel, copper, aluminum and brass.

16. Apparatus according to claim 1, said first electrode is embedded with its free surface in a potting compound.

17. Apparatus according to claim 16, wherein said first electrode is vapor-deposited on the potting compound.

18. Apparatus comprising to claim 2, wherein said apparatus is formed in a parallelepipedic shape and said circuit part, said electrodes and said insulator plate arranged therein; said ionization means of the apparatus also having walls formed by one of said electrodes into a protective basket and being grounded.

19. Apparatus according to claim 1, wherein a circuit is arranged in said circuit part and comprises a converter which transforms a main voltage to the voltage applied to said electrodes.

20. Apparatus according to claim 19, wherein said main voltage is 220V a.c. or 24V d.c. and said transformed voltage is a multiple value thereof.

21. Apparatus according to claim 20, wherein said transformed voltage is 3 kV. a.c. or 3kV d.c.

22. Apparatus according to claim 19, wherein said circuit further includes a chopper circuit provided for producing the frequency for said converter.

23. Apparatus according to claim 6, wherein said second electrode forms a cover of parallelepipedic shape and is provided with perforated walls.

24. In an apparatus for sterilizing and deodorizing rooms, including rooms having space inside cooled by refrigeration, comprising an ionization part having an insulator and two facing electrodes mounted to said insulator, and having a circuit part for producing high voltage and high frequency applied to said electrodes for producing a corona discharge, the improvement
  wherein at least the circuit pat for producing high voltage and high frequency being embedded in a potting compound;
  wherein said ionization part and circuit part are formed in a parallelepipedic shape and said circuit part, said electrodes and said insulator plate being arranged therein; and
  further wherein said ionization means has walls formed by one of said electrodes into a protective basket which is grounded.

25. In an apparatus for sterilizing and deodorizing rooms including rooms having space inside cooled by refrigeration, comprising an insulator and two facing electrodes mounted to said insulator, and a circuit part for producing high voltage and high frequency applied to said electrodes for producing a corona discharge, the improvement
  wherein at least the circuit part for producing high voltage and high frequency being embedded in a potting compound;
  wherein said insulator is a substantially planar insulator plate having mounted on one side a first electrode made from metal and having mounted on the other side a second electrode also made from metal; and
  further wherein said second electrode forms a cover of parallelepipedic shape and is provided with perforated walls.

* * * * *